US009580502B2

(12) United States Patent
Goldstein

(10) Patent No.: US 9,580,502 B2
(45) Date of Patent: Feb. 28, 2017

(54) COMPOSITIONS FOR SELECTIVE REDUCTION OF CIRCULATING BIOACTIVE SOLUBLE TNF AND METHODS FOR TREATING TNF-MEDIATED DISEASE

(71) Applicant: Thymon, LLC, New York, NY (US)

(72) Inventor: Gideon Goldstein, New York, NY (US)

(73) Assignee: Thymon, LLC, New York, NY (US)

( * ) Notice: Subject to any disclaimer, the term of this patent is extended or adjusted under 35 U.S.C. 154(b) by 0 days.

(21) Appl. No.: 15/176,503

(22) Filed: Jun. 8, 2016

(65) Prior Publication Data
US 2016/0272705 A1    Sep. 22, 2016

Related U.S. Application Data

(60) Division of application No. 14/695,551, filed on Apr. 24, 2015, now Pat. No. 9,388,240, which is a continuation of application No. PCT/US2014/012686, filed on Jan. 23, 2014.

(60) Provisional application No. 61/768,044, filed on Feb. 22, 2013, provisional application No. 61/756,571, filed on Jan. 25, 2013.

(51) Int. Cl.
*A61K 39/395* (2006.01)
*C07K 16/24* (2006.01)
*C07K 14/525* (2006.01)

(52) U.S. Cl.
CPC .......... *C07K 16/241* (2013.01); *C07K 14/525* (2013.01); *C07K 2317/34* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 5,616,321 | A | 4/1997 | Hector et al. |
| 5,658,803 | A | 8/1997 | Kuo |
| 5,698,419 | A | 12/1997 | Wolpe et al. |
| 5,700,466 | A | 12/1997 | Wolpe et al. |
| 5,919,452 | A | 7/1999 | Le et al. |
| 6,090,382 | A | 7/2000 | Salfeld et al. |
| 6,235,281 | B1 | 5/2001 | Stenzel et al. |
| 6,579,697 | B1 | 6/2003 | Wallach et al. |
| 6,835,823 | B2 | 12/2004 | Le et al. |
| 7,070,775 | B2 | 7/2006 | Le et al. |
| 7,223,394 | B2 | 5/2007 | Salfeld et al. |
| 7,226,593 | B2 | 6/2007 | Le et al. |
| 7,227,003 | B2 | 6/2007 | Le et al. |
| 7,268,116 | B2 | 9/2007 | Liang |
| 7,691,815 | B2 | 4/2010 | Liang |
| 7,846,442 | B2 | 12/2010 | Feldmann et al. |
| 7,863,239 | B2 | 1/2011 | Timmerman et al. |
| 8,063,182 | B1 | 11/2011 | Brockhaus et al. |
| 8,318,172 | B2 | 11/2012 | Grunewald et al. |
| 8,859,739 | B2 | 10/2014 | Kontermann et al. |
| 2009/0022659 | A1* | 1/2009 | Olson ................ A61K 47/4843 424/1.49 |
| 2011/0052525 | A1 | 3/2011 | Grunewald et al. |
| 2011/0195063 | A1 | 8/2011 | Le et al. |
| 2012/0251547 | A1 | 10/2012 | Tocker et al. |
| 2014/0165223 | A1 | 6/2014 | Ntouni et al. |

FOREIGN PATENT DOCUMENTS

| | | |
|---|---|---|
| CN | 101214372 | 7/2008 |
| EP | 2327723 | 6/2011 |
| WO | WO 93/01211 | 1/1993 |
| WO | WO 2005/117940 | 12/2005 |
| WO | WO 2007/064997 | 6/2007 |
| WO | WO 2008/144753 | 11/2008 |
| WO | WO 2012/018284 | 2/2012 |
| WO | WO 2014/116789 | 7/2014 |
| WO | WO 2014/123696 | 8/2014 |

OTHER PUBLICATIONS

Marusic et al., The Journal of Biological Chemistry vol. 287, No. 11, pp. 8613-8620, Mar. 9, 2012.*
Bodmer, J. et al., The Molecular Architecture of the TNF Superfamily., Trends in Biochemical Sciences, Jan. 2002, 27(1): 19-26.
Socher, S.H., et al. Antibodies against amino acids 1-15 of tumor necrosis factor block its binding to cell-surface receptor. Proceedings of the National Academy of Sciences of the United States of America, Aug. 1987, 84: 8829-8833.
Smith, R.A. & Baglioni, C. The active form of tumor necrosis factor is a trimer. The Journal of biological chemistry, May 1987, 262: 6951-6954.
Eck, M.J. & Sprang, S.R. The structure of tumor necrosis factor-alpha at 2.6 A resolution. Implications for receptor binding. The Journal of biological chemistry, May 1989, 264: 17595-17605.

(Continued)

*Primary Examiner* — Zachary Skelding
(74) *Attorney, Agent, or Firm* — Howson & Howson LLP

(57) ABSTRACT

An isolated or synthetic antibody or ligand is provided that specifically binds to an epitope of a dissociated monomer of human TNF. Such binding disrupts assembly of the monomer into bioactive trimeric human sTNF. A pharmaceutical composition contains one or more antibodies or ligands: (a) an antibody or ligand that specifically binds the TNF monomer-specific epitope having the sequence PSDKPVAH or PSDKPVAHV, amino acids 8-15 or 8-16 of SEQ ID NO: 1; and (b) an antibody or ligand that specifically binds the TNF monomer-specific epitope having the sequence EPIYLG-GVF, amino acids 116 to 124 of SEQ ID NO: 1. A combination of antibodies or ligands that bind or are reactive with (a) and/or (b) are useful in methods for treating a subject having a disease (e.g., rheumatoid arthritis, ankylosing spondylitis, juvenile rheumatoid arthritis, psoriatic arthritis, atherosclerosis, metabolic syndrome, Alzheimer's Disease, HIV, Type II diabetes) mediated by human TNF. These methods and compositions disrupt or reduce the in vivo assembly or reassembly of dissociated monomers of TNF into bioactive trimeric human sTNF.

8 Claims, 9 Drawing Sheets

(56) References Cited

OTHER PUBLICATIONS

Yamamoto, R., et al., Histidine-15: an important role in the cytotoxic activity of human tumor necrosis factor. Protein engineering, May 1989, 2: 553-558.

Zhang, X.M., et al., Site-directed mutational analysis of human tumor necrosis factor-alpha receptor binding site and structure-functional relationship. The Journal of Biological Chemistry, Nov. 1992, 267: 24069-24075.

Corti, A., et al. Oligomeric tumour necrosis factor alpha slowly converts into inactive forms at bioactive levels. The Biochemical Journal, Jun. 1992, 284: 905-910.

Chackerian, B., et al., Conjugation of a self-antigen to papillomavirus-like particles allows for efficient induction of protective autoantibodies. The Journal of Clinical Investigation, Jun. 2001, 108: 415-423.

Steed, P.M., et al. Inactivation of TNF signaling by rationally designed dominant-negative TNF variants. Science, Sep. 2003, 301: 1895-1898.

Zalevsky, J., et al. Dominant-negative inhibitors of soluble TNF attenuate experimental arthritis without suppressing innate immunity to infection. J Immunol, Mar. 2007, 179: 1872-1883.

Spohn, G., et al. A virus-like particle-based vaccine selectively targeting soluble TNF-alpha protects from arthritis without inducing reactivation of latent tuberculosis. J Immunol, Jan. 2007, 178: 7450-7457.

Yone, K et al, "Epitopic Regions for Antibodies against Tumor Necrosis Factor Alpha", J. Biol. Chem., Aug. 1995, 270(33):19509-19515.

McCoy, MK & Tansey, MG, TNF Signaling Inhibition in the CNS: Implications for Normal Brain Function and Neurodegenerative Disease J. Neuroinflam, Aug. 2008, 5(45).

Carlino, J.A. et al., Use of a Sensitive Receptor Binding Assay to Discriminate between Full-Length and Truncated Human Recombinant Tumor Necrosis Factor Proteins, The Journal of Biological Chemistry, Oct. 1986, 262(3): 958-961.

Goh, C.R. and Porter, A.G., Structural and Functional Domains in Humor Tumour Necrosis Factors, Protein Engineering, Apr. 1991, 4(4): 385-389.

Junghans, R.P. and Anderson, C.L., The protection receptor for IgG catabolism is the beta2-microglobulin-containing neonatal intestinal transport receptor, Proceedings of the National Academy of Sciences of the United States of America, May 1996, 93(11): 5512-5516.

Keane, J., TNF-Blocking Agents and Tuberculosis: New Drugs Illuminate an Old Topic, Rheumatology, Jan. 2005, 44: 714-720.

Le Buanec, H. et al., TNF kinoid vaccination-induced neutralizing antibodies to TNF protect mice from autologous TNF-driven chronic and acute inflammation, Proceedings of the National Academy of Sciences, Dec. 2006, 103(51): 19442-19447.

Lehmann, V. et al., Lethal toxicity of lipopolysaccharide and tumor necrosis factor in normal and D-galactosamine-treated mice, The Journal of Experimental Medicine, Mar. 1987, 165(3): 657-663.

Remicade Package Insert, Oct. 2011.

Wingfield, P. et al., Tumour Necrosis Factor is a Compact Trimer, FEBS Letters, Jan. 1987, 211(2): 179-184.

Ardestani, S. et al., Membrane versus Soluble Isoforms of TNF-a Exert Opposing Effects on Tumor Growth and Survival of Tumor-Associated Myeloid Cells, Cancer Research, May 2013, 73: 3938-3950.

Hess, A. et al., Blockade of TNF-α rapidly inhibits pain responses in the central nervous system, Proceedings of the National Academy of Sciences of the United States of America, Mar. 2011, 108(9): 3731-373.

Alexopoulou, L., et al. Transmembrane TNF protects mutant mice against intracellular bacterial infections, chronic inflammation and autoimmunity. European Journal of immunology, Aug. 2006, 36(10): 2768-2780.

Bongartz, T., et al. Anti-TNF antibody therapy in rheumatoid arthritis and the risk of serious infections and malignancies: systematic review and meta-analysis of rare harmful effects in randomized controlled trials. JAMA : the Journal of the American Medical Association, May 2006, 295(19): 2275-2285.

Douni, E., et al. A RANKL G278R mutation causing osteopetrosis identifies a functional amino acid essential for trimer assembly in RANKL and TNF. Human Molecular Genetics, Feb. 2012, 21(4): 784-798.

Fee, C. J., Protein conjugates purification and characterization, PEGylated Protein Drugs: Basic Science and Clinical Applications, Veronese, F. M., Ed. Birkhauser Publishing: Basel, 2009, 113-125.

Feldmann, M. & Maini, R.N. Anti-TNF therapy, from rationale to standard of care: what lessons has it taught us? J Immunol, Jul. 2010, 185(2): 791-794.

Goldstein, G. and Chicca, JJ, A universal anti-HIV-1 Tat epitope vaccine that is fully synthetic and self-adjuvanting vaccine., Vaccine, Dec. 2009, 28(4): 1008-1014.

He, M.M., et al. Small-molecule inhibition of TNF-alpha. Science, Jul. 2005, 310(5750): 1022-1025.

Li, Q., et al. Mechanism of action differences in the antitumor effects of transmembrane and secretory tumor necrosis factor-alpha in vitro and in vivo. Cancer immunology, Immunotherapy : CII, Dec. 2006, 55(12): 1470-1479.

Martin, JS and Zhu, Z, Recombinant approaches to IgG-like bispecific antibodies, Acta Pharmacologica Sinica, Jun. 2005, 26(6): 649-658.

Mitoma, H., et al. Infliximab induces potent anti-inflammatory responses by outside-to-inside signals through transmembrane TNF-alpha. Gastroenterology, Feb. 2005, 28(2): 376-392.

Mukai, Y., et al. Solution of the structure of the TNF-TNFR2 complex. Science Signaling, Nov. 2010, 3(148).

Nagahira, K., et al. Epitope mapping of monoclonal antibodies to tumor necrosis factor-alpha by synthetic peptide approach. Immunology Letters, May 1995, 46(1-2): 135-141.

Olleros, M.L., et al. Transmembrane TNF induces an efficient cell-mediated immunity and resistance to Mycobacterium bovis bacillus Calmette-Guerin infection in the absence of secreted TNF and lymphotoxin-alpha. J Immunol, Apr. 2002, 168(7): 3394-3401.

Scallon, B.J., et al., Chimeric anti-TNF-alpha monoclonal antibody cA2 binds recombinant transmembrane TNF-alpha and activates immune effector functions. Cytokine, Apr. 1995, 7(3): 251-259.

Speiss, C. et al, Bispecific antibodies with natural architecture produced by co-culture of bacteria expressing two distinct half-antibodies, Nature Biotechnology, Aug. 2013, 31(8): 753-758.

Stacy, AR et al, Induction of a Striking Systemic Cytokine Cascade prior to Peak Viremia in Acute Human Immunodeficiency Virus Type 1 Infection, in Contrast to More Modest and Delayed Responses in Acute Hepatitis B and C Virus Infections, J. Virol., Apr. 2009, 83(8): 3719-3733.

Tabas, I. and Glass, CK, Anti-inflammatory Therapy in Chronic Disease: Challenges and Opportunities., Science, Jan. 2013, 339(6116): 166-172.

Tang, P., et al., Human pro-tumor necrosis factor is a homotrimer. Biochemistry, Jun. 1996, 135(25): 8216-8225.

Utsumi, T., et al. Transmembrane TNF (pro-TNF) is palmitoylated. FEBS Letters, Jun. 2001, 500(1): 1-6.

Van Ostade, X., et al., Localization of the active site of human tumour necrosis factor (hTNF) by mutational analysis. The EMBO Journal, Apr. 1991, 10(4): 827-836.

Wallis, R.S., et al., Granulomatous infectious diseases associated with tumor necrosis factor antagonists. Clinical infectious diseases : an official publication of the Infectious Diseases Society of America, May 2004, 38(9): 1261-1265.

Wells, J.A. & McClendon, C.L. Reaching for high-hanging fruit in drug discovery at protein-protein interfaces. Nature, Dec. 2007, 450(7172): 1001-1009.

Yang, Z., et al., Crystal structure of TNFalpha complexed with a poxvirus MHC-related TNF binding protein. Nature Structural & Molecular Biology, Nov. 2009, 16(11): 1189-1191.

Song M.Y, et al. "Characterization of a novel anti-human TNF-alpha murine monoclonal antibody with high binding affinity and neutralizing activity", Exp. Mol. Med., Feb. 2008, 40(1):35-42.

Fox D.A "Cytokine blockade as a new strategy to treat rheumatoid arthritis: inhibition of tumor necrosis factor", Arch. Intern. Med., Feb. 2000, 160(4):437-444.

(56) References Cited

OTHER PUBLICATIONS

Scallon B, et al. "Binding and functional comparisons of two types of tumor necrosis factor antagonists", J. Pharmacol. Exp. Ther., May 2002, 301(2):418-426.
Adolf G.R and Fruhbeis B., "Monoclonal antibodies to soluble human TNF receptor (TNF binding protein) enhance its ability to block TNF toxicity", Cytokine, May 1992, 4(3):180-184).
Meager A., et al., "Preparation and characterization of monoclonal antibodies directed against antigenic determinants of recombinant human tumour necrosis factor (rTNF)", Hybridoma, Jun. 1987, 6(3):305-311.
Humira Drug Insert, Dec. 20, 2012.
Grunewald, J. et al., Immunochemical termination of self-tolerance, Proceedings of the National Academy of Sciences of the United States of America, Aug. 2008, 105(32):11276-11280.
Taylor, P.C. & Feldmann, M. Anti-TNF biologic agents: still the therapy of choice for rheumatoid arthritis. Nature reviews. Rheumatology 5, 578-582 (2009).
La Rosa, C. et al., Clinical Evaluation of Safety and Immunogenicity of PADRE-Cytomegalovirus (CMV) and Tetanus-CMV Fusion Peptide Vaccines With or Without PF03512676 Adjuvant, Journal of Infectious Disease, Apr. 2012, 205(8): 1294-1304.
Shibata, H. et al., Creation and X-Ray Structure Analysis of the Tumor Necrosis Factor Receptor-l-Selective Mutant of a Tumor Necrosis Factor Antagonist, The Journal of Biological Chemistry, Jan. 2008, 283(2): 998-1007.
Vandepapeliere, P. et al., Safety, Immunogenicity and Clinical Phase I-II Results of TNF-alpha-Kinoid Immunotherapeutic in Crohn's Disease Patients, Gastroenterology, 2011, 140:S-123.
CN 101214372 English Translation from Espacenet downloaded on Oct. 28, 2015.
International Search Report issued Mar. 14, 2014 in corresponding International Patent Application No. PCT/US14/12686 (international stage of present application).

Written Opinion issued Mar. 14, 2014 in corresponding International Patent Application No. PCT/US14/12686 (international stage of present application).
International Search Report issued Apr. 11, 2014 in related International Patent Application No. PCT/US14/12678.
Written Opinion issued Mar. 14, 2014 in related International Patent Application No. PCT/US14/12678.
International Preliminary Report on Patentability for corresponding International Patent Application No. PCT/US2014/012686 filed Jan. 23, 2014.
International Preliminary Report on Patentability for related International Patent Application No. PCT/US2014/012678 filed Jan. 23, 2014.
Office Action dated Nov. 2, 2015 in related U.S. Appl. No. 14/695,807, filed Apr. 24, 2015.
Office Action and Translation dated Mar. 14, 2016 in corresponding Chinese Application No. 2014800006055.1, filed Jul. 24, 2015.
Dong, J. et al., The Protective Antibodies Induced by a Novel Epitope of Human TNF-(alpha) Could Suppress the Development of Collagen-Induced Arthritis, Plos One, Jan. 2010, 5(1): e8920.
Corti, A. et al., Antigenic Regions of Tumor Necrosis Factor Alpha and Their Topographic Relationships with Structural/Functional Domains, Mol. Immunol, Sep. 1991, 29(4):471-479.
Response to Office Action of Mar. 14, 2016 corresponding Chinese Application No. 2014800006055.1 in Chinese, and English translation of arguments with translated claims.
Office Action dated Jun. 21, 2016 in corresponding Canadian Patent Application No. 2,898,354, filed Jul. 15, 2015.
Office Action dated Jul. 8, 2016 in corresponding European Patent Application No. 14749653.3.
Office Action dated Jun. 16, 2016 in corresponding Australian Patent Application No. 2014215639.
Office Action dated Aug. 3, 2016 in corresponding Japanese Patent Application No. 2015-555264.

* cited by examiner

FIG. 1

TNF Interface A (underlined)

Immunogen:

TNF 1-23 VRSSSRTPSDKPVAHVVANPQAE

Epitopes detected:

A1:   TNF 4-12 SSRTPSDKP

A2:   TNF 8-15 (in rats)    PSDKPVAH

A2:   TNF 8-16 (in mouse) PSDKPVAHV

TNF Interface F (underlined)

Immunogen:

TNF 112-128 KPWYEPIYLGGVFQLEK

Epitope detected: TNF 116-124 EPIYLGGVF

FIG. 2C

F epitope margins

[Bar chart showing Titer vs TNF peptides:
- 118-124 IYLGGVF: ~5,000
- 117-124 PIYLGGVF: ~18,000
- 116-124 EPIYLGGVF: ~54,000
- 116-123 EPIYLGGV: 0]

Sandwich of Epitope A1 and A2 Antiserum

--●-- Remicade

--○-- Protein A/G purified IgG from TNF 1-23 immunization (A1/A2)

FIG. 4A

Epitope A1 and A2 Rat Antiserum to TNF 1-23
Inhibition of TNF Cytotoxicity $P < 0.0001$, one way ANOVA Titers of anti-TNF antiserum with TNF in all wells (x-axis: 1,000,000; 250,000; 100,000; 25,000; 10,000; 2,500; 50% NRS + TNF)

Dunnett's post testing
** $P < 0.0001$; * $P < 0.001$; **** $P < 0.0001$; NS not significant

FIG. 4B

Inhibition of TNF Cytotoxicity
in WEHI Cells, MTT Assay, by
Antiserum to F Interface
Immunogen Dunnett's multiple comparisons versus TNF alone
 $P < 0.01$, ** $P < 0.0001$

SEQUENCE LISTING

<160> NUMBER OF SEQ ID NOS: 1

<210> SEQ ID NO 1
<211> LENGTH: 157
<212> TYPE: PRT
<213> ORGANISM: Homo sapiens

<400> SEQUENCE: 1

```
Val Arg Ser Ser Ser Arg Thr Pro Ser Asp Lys Pro Val Ala His Val
1               5                   10                  15

Val Ala Asn Pro Gln Ala Glu Gly Gln Leu Gln Trp Leu Asn Arg Arg
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Lys Gly Gln Gly Cys Pro Ser Thr His Val Leu Leu Thr His Thr Ile
65                  70                  75                  80

Ser Arg Ile Ala Val Ser Tyr Gln Thr Lys Val Asn Leu Leu Ser Ala
                85                  90                  95

Ile Lys Ser Pro Cys Gln Arg Glu Thr Pro Glu Gly Ala Glu Ala Lys
            100                 105                 110

Pro Trp Tyr Glu Pro Ile Tyr Leu Gly Gly Val Phe Gln Leu Glu Lys
        115                 120                 125

Gly Asp Arg Leu Ser Ala Glu Ile Asn Arg Pro Asp Tyr Leu Asp Phe
    130                 135                 140

Ala Glu Ser Gly Gln Val Tyr Phe Gly Ile Ile Ala Leu
145                 150                 155
```

COMPOSITIONS FOR SELECTIVE REDUCTION OF CIRCULATING BIOACTIVE SOLUBLE TNF AND METHODS FOR TREATING TNF-MEDIATED DISEASE

CROSS-REFERENCE TO RELATED APPLICATIONS

This application is a divisional application of pending U.S. patent application Ser. No. 14/695,551, filed on Apr. 24, 2015, which is a continuation of international patent application No. PCT/2014/12686, filed on Jan. 23, 2014, which claims priority of U.S. provisional patent application No. 61/768,044, filed Feb. 22, 2013 and U.S. provisional patent application No. 61/756,571, filed Jan. 25, 2013. All patent applications are incorporated herein by reference.

INCORPORATION-BY REFERENCE OF MATERIAL SUBMITTED IN ELECTRONIC FORM

Applicant hereby incorporates by reference the Sequence Listing material filed in electronic form herewith. This file is labeled GGP11PCT_ST25.txt", was created on Jan. 23, 2014, and is 2 KB in size.

BACKGROUND OF THE INVENTION

Tumor necrosis factor (TNF; previously referred to as tumor necrosis factor-α) is a proinflammatory cytokine that plays a major role in the pathogenesis of rheumatoid arthritis and associated inflammatory diseases, such as ankylosing spondylitis, juvenile rheumatoid arthritis, and psoriatic arthritis. The human proform, transmembrane-bound TNF (tmTNF), is a 26-kDa homotrimer comprising three non-covalently associated monomers, each monomer having N-terminal sequence imbedded in the cell membrane. Each monomer of tmTNF has a 233 amino acid sequence (UniProtKB/Swiss-Prot entry Accession No. P01375). Soluble TNF (sTNF) is a homotrimer formed by enzymatic cleavage from its pro-form tmTNF. Each monomer of the sTNF trimer has a 157 amino acid sequence (SEQ ID NO: 1), which is the same sequence as aa77 to 233 of the published Acc No. P01374.

Both forms of active TNF (tmTNF and sTNF) exist as homotrimers[10-13] and engage trimeric receptors that recognize receptor-binding sites in the grooves between the TNF monomers in assembled homotrimers. The grooves between the monomers comprise amino acid sequence from two contiguous monomers[14,15]. The receptor binding regions of both forms of TNF are identical.

Trimer integrity is essential for biological function. For tmTNF, trimeric structure is established intracellularly before tmTNF insertion into the cell membrane [16] and is maintained in tmTNF by the anchoring of the protein stems passing through the membrane plus further lipid anchoring by palmitoylated amino acid side chains at the membrane boundary[17]. In contrast, sTNF active trimers dissociate freely into inactive monomers SEQ ID NO: 1 and dimers that reform as active sTNF homotrimers in a steady-state equilibrium between the three forms[18].

Anti-TNF biologics have provided a major advance in the management of the above-noted inflammatory diseases with anti-TNF monoclonal antibodies REMICADE (Infliximab; Janssen Biotech, Inc.) and HUMIRA (Adalimumab, Abbott Laboratories), and a chimeric solubilized TNF receptor fused to Fc, i.e., ENBREL (Entanercept, Biogen, Inc) being widely used[1,2]. This therapeutic and marketing success is marred by the rare but statistically significant occurrence of serious infections and malignancies[3,4], likely related to concomitant blockade of tmTNF[5,6] function impairing immune defenses. These adverse occurrences have included the development of tuberculosis, systemic fungal infection and other intracellular infections due principally to intracellular pathogens such as *Mycobacterium tuberculosis, Listeria monocytogenes* and *Histoplasma capsulatum*, and certain forms of cancer. These results were unsurprising since these agents block pro-inflammatory sTNF but also block tmTNF, which is essential for juxtacrine cellular control of such intracellular infections and malignancies[3,7,9].

Because the receptor binding regions of both forms of TNF are identical, there has been little hope for the development of new monoclonal antibodies selectively blocking receptor engagements of one form versus the other. Antibodies to short sequences of TNF have not lead to useful therapeutics. For example, in 1987, Socher et al.[26] in exploring antibodies to full or partial synthetic sequences of TNF, observed a high polyclonal antibody response to the TNF fragment 1-15 that appeared to block bioactivity and receptor binding of TNF. However, this 16-year old observation has not lead to the development of additional therapeutic reagents, likely because the TNF receptor is a discontinuous surface region not associated with TNF amino acids 1-15. Subsequent researchers in 2001 coupled TNF amino acids 4-23 conjugated to papillomavirus-like particles, and observed an induction of polyclonal antibodies, and an attenuation of experimental arthritis[27]. Other researchers in 2007 used the same fragment TNF aa4-23 coupled to a virus-like particle-based composition and induced antibodies that attenuated experimental arthritis. No suppression of resistance to infection occurred, in contrast with full length TNF immunization[28]. Because these TNF fragments were not directed to receptor binding regions of TNF, these publications displayed no further teachings or suggestion of therapeutic use of the resulting polyclonal antibodies; and further research has not been published since that date.

One more recent attempt to selectively suppress the pro-inflammatory activity of sTNF while preserving tmTNF function required for innate immunity involved the design of synthetic dominant-negative TNF monomer variants that formed trimers that were inactive[19]. These were shown to attenuate experimental arthritis without suppressing innate immunity to infection[20], emphasizing the major role of sTNF in pathogenesis of arthritis. Another approach has been the search for small-molecule drugs that interact with the inter-monomer contact regions. One molecule, SP304, bound such a contact region with µM affinity to effect trimer disruption in vitro[21,22].

Despite the plethora of literature in the field of anti-TNF treatment for a variety of inflammatory disorders, there remains a need in the art for new and useful compositions and methods for generating therapeutic or prophylactic immunogenic compositions for these diseases which do not result in adverse side effects due to suppression of cellular immunity.

SUMMARY OF THE INVENTION

As described herein the inventor has provided selective anti-TNF monomer-specific biologic compositions and various methods of use thereof which do not affect the structure or bioactivity of tmTNF or increase the treated subject's susceptibility to infection by an intracellular pathogen.

In one aspect, an isolated or synthetic antibody or ligand is provided that specifically binds to an epitope of a dissociated monomer of human TNF. The binding of the antibody or ligand to the monomer disrupts or prevents assembly of the monomer into bioactive trimeric human sTNF. In one embodiment, the antibody or ligand binds specifically to monomer-specific epitope A2 of sequence PSDKPVAH, amino acids 8-15 of SEQ ID NO: 1 or PSDKPVAHV, amino acids 8-16 of SEQ ID NO: 1. In still another embodiment, the antibody or ligand binds specifically to monomer-specific epitope F of sequence EPIYLGGVF, amino acids 116 to 124 of SEQ ID NO: 1. In one embodiment, the antibody is a bi-specific antibody directed to epitopes A2 and F.

In another aspect, a pharmaceutical composition comprises one or more isolated or synthetic antibody or ligand that specifically binds to an epitope of a dissociated monomer of human TNF, the binding disrupting or preventing assembly of the monomer into bioactive trimeric human sTNF, and a pharmaceutically acceptable carrier or diluent. In certain embodiments, the composition contains one or two of the above-described antibodies.

In yet a further aspect, methods for preparing or generating isolated or synthetic antibodies or ligands that specifically bind to an epitope of a dissociated monomer of human TNF are provided.

In still another aspect, a method for treating a subject having a disease mediated by soluble human TNF (sTNF) comprises reducing the amount, concentration or bioactivity of sTNF in the blood of a subject having the disease without affecting the amount, concentration or bioactivity of tmTNF. This is accomplished by disrupting, preventing or reducing the in vivo assembly or reassembly of dissociated monomers of TNF into bioactive trimeric human sTNF without affecting the amount, concentration or bioactivity of tmTNF. In certain embodiments, this method employs the monomer-specific antibodies, bi-specific antibodies, ligands and compositions described above and herein. In one embodiment, the disease is rheumatoid arthritis (RA), juvenile rheumatoid arthritis, ankylosing spondylitis (AS), psoriatic arthritis or psoriasis.

In still another aspect, sTNF elevations are also implicated in initial HIV infection, and the reoccurrence of latent HIV infection and type II diabetes. Therefore, in still another aspect, a method for preventing a subject infected with HIV-1 and treated with anti-retroviral drugs from developing a new infection (or rebound infection due to latent HIV) comprises administering to the subject treated with anti-retroviral therapy (ART) with an isolated or synthetic selective anti-TNF monomer-specific antibody or ligand, or pharmaceutical composition, as described herein, after the ART is discontinued.

In yet another aspect, a method for treating a subject with type II diabetes comprises administering periodically to a subject in need thereof an isolated or synthetic selective anti-TNF monomer-specific antibody or ligand, or pharmaceutical composition, as described above, optionally in combination with known anti-diabetic therapies.

In other aspects, the TNF monomer-specific antibodies, ligands, bi-specific antibodies, or compositions described herein are provided for use in the treatment of a disease or disorder mediated by soluble human TNF, including any disease identified herein. In other aspects, use of the antibodies, ligands, or compositions described herein in preparation of a medicament for treatment of a disease or disorder mediated by soluble human TNF, including any disease identified herein, is provided.

Other aspects and advantages of these methods and compositions are described further in the following detailed description.

BRIEF DESCRIPTION OF THE DRAWINGS

FIG. 1 illustrates the immunogen and epitope detector sequences for TNF interface A and TNF Interface F, which were used to identify the sequences and margins of the three monomer-specific TNF epitopes A1, A2 and F described herein as well as the binding activities of the anti-TNF monomer-specific antibodies generated thereto. These sequences are discussed in Example 1 below.

FIG. 2C is a bar graph illustrating the results of determining the margins of the monomer-specific TNF epitopes by immunizing a rat or mouse with sTNF amino acids 112-128 of SEQ ID NO: 1, KP<u>WYEPIYLGGVF</u>QLEK (interface region underlined; F epitope in bold). Antibody binding responses were measured on recombinant TNF (rTNF), a mixture of monomers, dimers and trimers, and on synthetic peptides employing the indicated four terminally truncated TNF peptides. The synthetic peptides were IYLGGVF, amino acids 118-124 of SEQ ID NO: 1; PIYLGGVF, amino acids 117-124 of SEQ ID NO: 1, EPIYLGGVF, amino acids 116-124 of SEQ ID NO: 1 (epitope F) and EPIYLGGV, amino acids 116-123 of SEQ ID NO: 1. The greatest binding was to the aa116-124 peptide, thereby indicating the margins of the epitope (referred to as epitope F).

FIG. 4A illustrates the results of an assay of antibody inhibition of sTNF-induced cytotoxicity in target cells, using antiserum generated to TNF amino acids 1-23 that contains antibodies that selectively bind the monomer specific epitopes PSDKPVAH and SSRTPSDKP (epitopes A2 and A1, respectively). The titers of antisera with 200 pg/mL TNF in all wells are displayed under the bars, from $1 \times 10^6$, $2.5 \times 10^5$, $1 \times 10^5$, $2.5 \times 10^4$, $1 \times 10^4$, and $2.5 \times 10^3$. The last bar is sTNF in 50% NRS.

FIG. 4B illustrates functional blocking of sTNF cytotoxicity in actinomycin-treated WEHI cells in the assay described in Example 2 by antiserum to TNF epitope F. The indicated dilutions (50%, 16.7%, 5.6%, 1.85%, 0.48%) of monomer-specific antisera generated to the immunogen KPWYEPIYLGGVFQLEK, amino acids 112-128 of SEQ ID NO: 1 (the F beta sheet interface sequence of TNF), in rats were compared for their ability to inhibit sTNF bioactivity with 200 pg/mL TNF and 50% NRS (normal rat serum). As is shown in this figure, inhibition of TNF cytotoxicity was shown using antiserum diluted from 0.48% to 50%. Thus, the monomer-specific antisera to epitope F showed the ability to inhibit the cytotoxic effect of sTNF on the cells as evidenced by increasing replication of cells in the presence of the antisera. Statistical significance was determined by one-way ANOVA and post testing with Dunnett's test. REMICADE antibody, which binds trimeric TNF, was used as a positive control in this assay.

DETAILED DESCRIPTION OF THE INVENTION

Figure 2A:
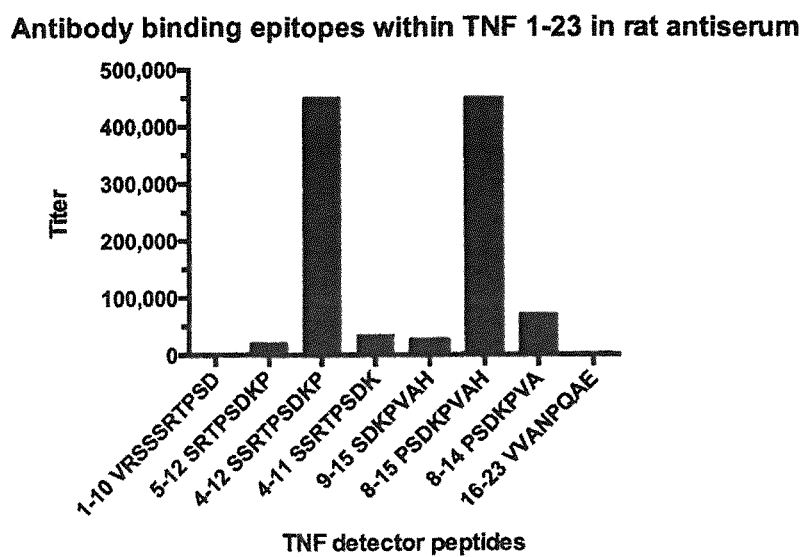
FIG. 2A is a bar graph illustrating the TNF monomer-specific epitopes by immunizing a rat with sTNF amino acids 1-23. Antibody binding responses were measured on recombinant TNF (rTNF), a mixture of monomers, dimers and trimers, and on synthetic peptides employing the indicated terminally truncated TNF peptides. The synthetic detector peptides included: TNF amino acids 1-10 of SEQ ID NO: 1, which demonstrated no binding at all; TNF amino acids 5-12 of SEQ ID NO: 1, minimal to no binding; the A1 epitope SSRTPSDKP, TNF amino acids 4-12 of SEQ ID NO: 1; TNF amino acids 4-11 of SEQ ID NO: 1 SSRTPSDK; TNF amino acids 9-15 of SEQ ID NO: 1 SDKPVAH; the A2 epitope sequence of amino acids 8-15 of SEQ ID NO: 1; TNF amino acids 8-14 of SEQ ID NO: 1 PSDKPVA; and TNF amino acids 16-23 of SEQ ID NO: 1 VVANPQAE, which exhibited no binding. Clearly only two overlapping epitopes were detected by rat antiserum to TNF amino acids 1-23, which were epitope A1, TNF amino acids 4-12 and A2, TNF amino acids 8-15.
Figure 2B:
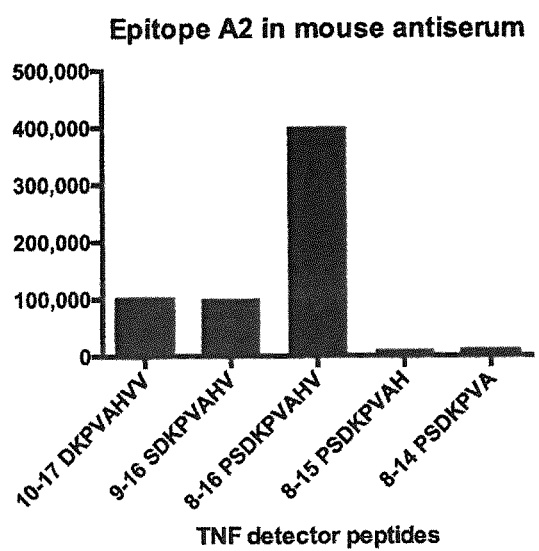
FIG. 2B is a bar graph illustrating the margins of the A2 epitope PSDKPVAHV detected in mouse serum using the same procedure described in FIG. 2A, with synthetic peptides. The synthetic detector peptides included: TNF amino acids 10-17 of SEQ ID NO: 1 DKPVAHVV, which demonstrated minimal binding; TNF amino acids 9-16, minimal binding; the A2 epitope PSDKPVAHV, TNF amino acids 8-16 of SEQ ID NO: 1; TNF amino acids 8-15 of SEQ ID NO: 1 PSDKPVAH; and TNF amino acids 8-14 of SEQ ID NO: 1 PSDKPVA, no binding. When rat and rabbit sera were used, the boundaries of epitope A2 are amino acids 8-15 of SEQ ID NO: 1. The immune system of the mouse sees only TNF amino acids 8-16 and does not bind to TNF amino acids 8-15, as shown in the graph.
Figure 3A:
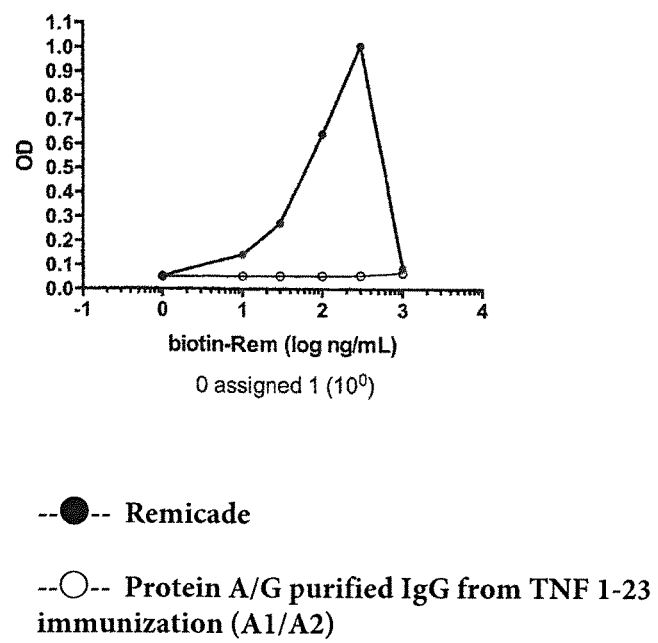
FIG. 3A illustrates data from the sandwich assay using 200 ng/mL sTNF, biotin-labeled antibody and non-biotin labeled antibody, as described in Example 2 below. The binding curves show that commercial REMICADE anti-TNF antibody, when labeled with biotin and mixed with sTNF (trimers, dimers and monomers), binds multimeric forms of TNF. The biotinylated antibody-TNF in the mixture still has available TNF trimer epitopes that can bind and form a sandwich with the unlabeled plated REMICADE antibody (●). In contrast, Protein A/Protein G purified IgG (○) was obtained from rats immunized with TNF amino acids 1-23 of SEQ ID NO: 1. This purified IgG contains a mixture of monomer-specific anti-TNF that selectively bind epitope A1 and monomer-specific anti-TNF that selectively bind epitope A2. The purified IgG (○) does not sandwich in the assay, because once these antibodies bind the TNF monomers in the TNF mixture, the labeled monomer-specific antibody-TNF complexes have no available monomer-specific epitopes to bind to the plated unlabeled monomer-specific antibody on the plate. Labeled TNF monomer-specific antibody-monomers complexes are simply washed from the plate without binding. REMICADE antibody that binds trimeric TNF was used as a positive control in this assay. Thus neither anti-A1 nor anti-A2 antibodies bind the trimeric form of sTNF.
Figure 3B:
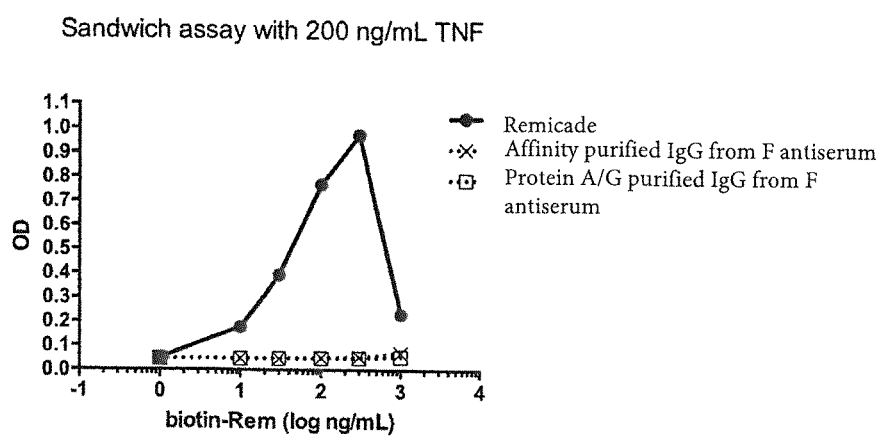
FIG. 3B illustrates data from a similar sandwich assay to that of FIG. 3A, using as reagents: commercial REMICADE anti-TNF antibody (●); affinity purified IgG from monomer-specific antisera to the TNF epitope F that selectively binds only epitope F: EPIYLGGVF (X) and Protein A/G purified IgG from monomer-specific antisera to the TNF epitope F that selectively binds only epitope F: EPIYLGGVF (□). Thus, in contrast to the commercial REMICADE anti-TNF antibodies, the anti-F antibodies do not bind the to trimeric form of sTNF.
Figure 5:
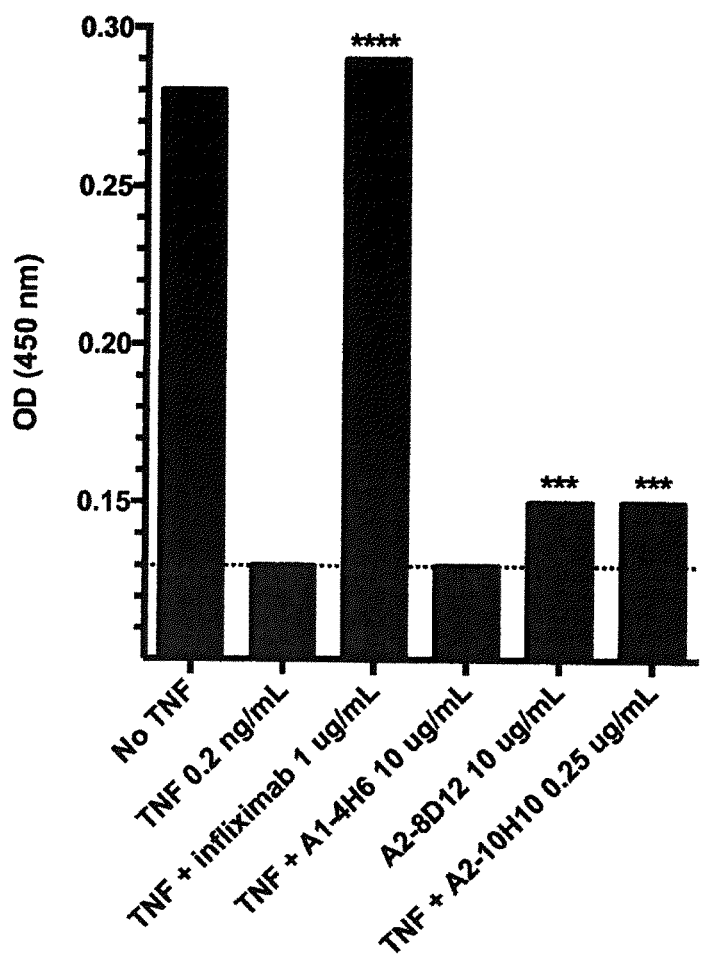
FIG. 5 is a bar graph showing inhibition of sTNF cytotoxicity in WEHI cells by monoclonal antibody generated to TNF epitopes A1 or A2. Cell replication (OD) was measured in WEHI cells grown in the presence of no TNF and the cells showed good replication. WEHI cells grown in the presence of 0.2 ng/ml full length TNF 1-157 of SEQ ID NO: 1 demonstrated that TNF inhibited replication. Cells grown in TNF plus the commercial REMICADE anti-TNF antibody at 1 μg/mL, showed that the antibody returned replication to the same levels demonstrated in the absence of TNF. TNF plus the inventor's monoclonal monomer-specific antibody A1-4H6 to TNF epitope A1 (amino acids 4-12 of SEQ ID NO: 1) at 10 μg/mL, failed to inhibit WEHI cell replication, which remained at the levels of cells exposed to TNF alone. WEHI cells were cultured in the presence of TNF plus the inventor's monomer-specific monoclonal antibody A2-8D12 to TNF epitope A2 (amino acids 8-16 of SEQ ID NO: 1) at 10 μg/mL; and TNF plus the inventor's monomer-specific monoclonal antibody A2-10H10 to TNF epitope A2 (amino acids 8-16 of SEQ ID NO: 1) at 0.25 μg/mL. Data from these two latter monomer-specific monoclonal antibodies showed highly statistically significant inhibition of sTNF cytotoxicity (i.e., reduction of cell killing). The second monomer-specific monoclonal antibody A2-10H10 showed high sensitivity, a 40× increase in potency in this assay over the other monomer-specific anti-A2 antibody A2-8D12. These results demonstrate that monomer-specific anti-A2 monoclonal antibodies inhibit sTNF and that one such antibody A2-10H10 exhibits a higher affinity than the other, as demonstrated by the 40 fold lower dose. No inhibition even at a high dose was demonstrated by the monomer-specific anti-A1 monoclonal antibody. These data demonstrate that the effects of the TNF amino acid 1-23 polyclonal antisera were due to the monomer-specific anti-A2 antibodies only.

The inventor has provided selective anti-TNF monomer-specific biologic compositions and various methods of use based on the determination that antibodies and/or other ligands directed to selected epitopes partially or fully within the internal interface contact region of TNF free monomers block their association with other monomers and cause progressive disruption of bioactive sTNF trimer formation. It is advantageous to have an antibody or ligand, e.g., a monoclonal antibody or bi-specific antibody, that selectively blocks the activity of sTNF but not tmTNF for the treatment of rheumatoid arthritis (RA), juvenile rheumatoid arthritis, ankylosing spondylitis (AS) and psoriatic arthritis (PA), psoriasis, and other inflammatory diseases.

I. Antibodies/Ligands

Thus, this invention provides an isolated or synthetic antibody or ligand that specifically binds to an epitope of a dissociated monomer of human TNF, the binding disrupting or preventing assembly of monomers into bioactive trimeric human sTNF.

The inventor determined that antibodies directed to certain epitopes partially or fully within the internal interface contact region of free TNF monomers would block their association with other monomers and cause progressive disruption of trimer formation. In contrast to the known publications on TNF, the inventor determined that there were two overlapping epitopes in the TNF sequence of amino acids 1-15 of SEQ ID NO: 1. One epitope A1 which spanned amino acids 4-12 of SEQ ID NO: 1 was monomer-specific, but did not disrupt trimer formation. The other epitope A2, which spanned amino acids 8-15 or 8-16 of SEQ ID NO: 1, was monomer-specific and did disrupt trimer formation. Further the inventor identified a new unrecognized epitope F, amino acids 116-124 of SEQ ID NO: 1 in the F β sheet of TNF, which was monomer-specific and did disrupt trimer formation. The discovery and new uses of antibodies or ligands that specifically bind these epitopes is discussed in detail below and in the examples.

Early x-ray crystallography studies established that the 157 amino acid (SEQ ID NO: 1) sTNF monomers formed an "elongated, anti-parallel β pleated sheet sandwich with "jelly-roll" topology". Three monomers in intimate but non-covalent association constituted the active trimer[11]. Five stretches of amino acid sequences formed the interface β sheet contact surfaces: A, aa11-18; A', aa35-39; C, aa54-67; F, aa114-126 and H, aa149-157, all of SEQ ID NO: 1, where A, A', C, F and H refer to a β sheet naming convention[11]. The inventor explored all five regions for potential B cell epitopes and detected and mapped antibodies to two epitopes partially (the A β sheet) and one epitope fully (the F β sheet) within an interface region, all being outside the known regions of the receptor binding sites of TNF[12,13,15]. See, Example 1 below.

In one embodiment, the selective anti-TNF monomer-specific antibody or ligand binds the epitope A2 of sequence PSDKPVAH, amino acids 8-15 of SEQ ID NO: 1 or sequence PSDKPVAHV, amino acids 8-16 of SEQ ID NO: 1. In another embodiment a selective anti-TNF monomer-specific antibody or ligand binds the A1 epitope of sequence SSRTPSDKP, amino acids 4-12 of SEQ ID NO: 1. In another embodiment, the TNF monomer-specific antibody or ligand binds the F epitope of sequence EPIYLGGVF, amino acids 116 to 124 of SEQ ID NO: 1.

As described below, antibodies to A1 epitope, while TNF monomer-specific, have been found to be inactive in blocking TNF function when used alone. Antibodies to these A2 and F epitopes specifically bind TNF monomers but not trimers, disrupt assembly of sTNF trimers and inhibit sTNF function in vitro. These monomer-specific anti-A2 and anti-F epitope antibodies or ligands do not bind transmembrane TNF (tmTNF) and do not affect the structure or bioactivity of tmTNF. Additionally, these antibodies or ligands do not bind intact bioactive trimeric human sTNF. Monoclonal antibodies to the A2 and F epitopes are useful for therapeutic use as safer sTNF-selective anti-TNF biologics for rheumatoid arthritis and related inflammatory diseases with sTNF-related pathologies.

As used herein, the term "antibody" refers to an intact immunoglobulin having two light and two heavy chains. The term "antibody fragment" refers to less than an intact antibody structure, including, without limitation, an isolated single antibody chain, an sc-Fv construct, a Fab construct, a $Fab_2$ construct, or a light chain variable or complementarity determining region (CDR) sequence, etc. The term "bi-specific" antibody refers to a synthetically or recombinantly produced antibody that contains one heavy and/or one light chain that binds to one epitope, e.g., the A2 epitope, and one heavy and/or one light chain that binds to a second epitope, e.g., the F epitope. The term "ligand" is used to refer to other synthetic molecules or sequences that can be designed to bind to the indicated epitopes.

"High affinity" is the strength of binding of the antibody or ligand in question to the TNF monomer-specific epitope A2 or F. In one embodiment, the antibodies/ligands to A2 or F bind at an affinity of less than 10 nanomolar (nM). In another embodiment, the antibodies/ligands to A2 or F bind at an affinity of less than 1 nanomolar (nM). In another embodiment, the antibodies/ligands to A2 or F bind at an affinity of less than 100 picomolar (pM). In another embodiment, the antibodies/ligands to A2 or F bind at an affinity of less than 10 pM.

Thus, in one embodiment, the antibody or ligand as described herein may be a polyclonal, affinity-purified or high affinity antibody or a fragment thereof. In one embodiment, the antibody or ligand is a monoclonal antibody or a fragment thereof. In another embodiment, the antibody or ligand is an isolated single chain of an antibody. Still other forms of antibodies, such as a synthetic antibody, a recombinant antibody, a chimeric antibody, a humanized antibody, a human antibody or a fragment thereof can be employed as the ligand or antibody directed to one of the above described epitopes. Suitable fragments of such antibodies may also be employed. In yet another embodiment, the antibody or ligand or fragment thereof further comprises a polyethylene glycol (PEG) molecule. The antibody or ligand or fragment can be associated or fused with PEG by known conventional methodologies.[30,31]

The production of antibodies or ligands that specifically bind to one of the selected epitopes, can employ conventional techniques. For example, polyclonal antibody compositions are typically produced by immunizing a selected mammal, e.g., a primate, rodent, or human, with a peptide/polypeptide composition containing a specific epitope. See, e.g., the description of the antisera described in FIGS. 2A-2C. The selection of high titer, high affinity polyclonal antibodies can be monitored by standard techniques, such as with an enzyme-linked immunosorbent assay and surface plasma resonance. If desired, the polyclonal antibody molecules can be isolated from the mammal, e.g., from the whole blood, plasma or serum, and further purified from the plasma or serum of the immunized mammal by conventional techniques. Conventional harvesting techniques can include plasmapheresis, protein A/G chromatography, among others. Such polyclonal antibody compositions may themselves be employed as pharmaceutical compositions of this invention.

Alternatively, monoclonal antibodies can be generated to any one of the epitopes by now conventional techniques, using antibody producing cells obtained from the immunized mammals and fused to non-IgG-producing myeloma cells to form hybridomas or from selection from activated immune B cells with extraction by known molecular biological techniques. These monoclonal antibodies can be further used to prepare other forms of antibodies and ligands, e.g., chimeric antibodies, humanized antibodies, human antibodies. Other antibody fragments or ligands can be produced by screening phage display libraries, antibody fragments and mixtures thereof. Techniques for generating these types of antibodies and ligands are well-known in the art and the ligands themselves may be generated using the disclosed amino acid sequences of the above-identified epitopes.[32,35-39]

Chimeric antibodies may similarly be developed using known techniques. Chimeric antibodies are molecules in which different portions are derived from different animal species. Single chain antibodies may also be prepared by conventional methods, such as described in U.S. Pat. Nos. 4,946,778 and 4,704,692 using the variable portions of the polyclonal or monoclonal antibodies produced according to this invention. Antibody fragments, such as the Fab, $F(ab)_2$ and scFv fragments and libraries thereof may also be employed in generation of the selective anti-TNF monomer-specific antibodies or ligands as described herein.

The production of bi-specific antibodies or ligands that specifically bind to two or more of the selected epitopes, can employ conventional techniques. It is within the skill of the art to develop bi-specific antibodies that bind multiple epitopes. See, e.g., Hornig N, Färber-Schwarz A., "Production of bispecific antibodies: diabodies and tandem scFv.", 2012, Methods Mol Biol., 907:713-27; Speiss, C. et al," Bispecific antibodies with natural architecture produced by co-culture of bacteria expressing two distinct half-antibodies, Jul. 7, 2013, Nature Biotechnology, 31:753-758; and Jonathan S Martin and Zhenping Zhu, "Recombinant approaches to IgG-like bispecific antibodies", 2005 Acta Pharmacologica Sinica, 26: 649-658. In one embodiment, a bispecific antibody is developed which is capable of binding to or reacting with epitope A2 and epitope F. It is anticipated that such bispecific antibodies, e.g., the antibody reactive with A2 and F, will enhance avidity and create greater potency than the single anti-A2 or anti-F antibodies or ligands alone.

Other selective anti-TNF monomer-specific antibodies or ligands may be developed by screening recombinant combinatorial immunoglobulin scFv libraries (e.g., phage displays) with one of the above-identified TNF monomer-specific epitopes to isolate immunoglobulin library members that bind to the TNF monomer. See, e.g., Phage Display of Peptides and Proteins, A Laboratory Manual., eds. Kay, B K et al, Elsevier Inc. (1996), among other texts well known in the art. Kits for generating and screening phage display libraries are commercially available, e.g., Pharmacia Recombinant Phage Antibody System, Catalog No. 27-9400-01; Stratagene Phage Display kits, etc. See, e.g., U.S. Pat. No. 5,223,409, International Publication No. WO92/09690, WO90/02809, etc.

II. Pharmaceutical Compositions

In another aspect, a pharmaceutical composition comprises an isolated or synthetic antibody or ligand that specifically binds to an epitope of a dissociated monomer of human TNF, the binding disrupting or preventing assembly of the monomer into bioactive trimeric human sTNF.

The pharmaceutical composition contains one or more of the selective anti-TNF monomer-specific antibodies or ligands described above with a suitable carrier or diluent. Thus, in one embodiment, the pharmaceutical composition contains an anti-TNF monomer-specific antibody or ligand that specifically binds the A2 epitope having the sequence PSDKPVAH, amino acids 8-15 of SEQ ID NO: 1 or PSDKPVAHV, amino acids 8-16 of SEQ ID NO: 1. In still another embodiment, the pharmaceutical composition contains a selective anti-TNF monomer-specific antibody or ligand that specifically binds the F epitope having the sequence EPIYLGGVF, amino acids 116 to 124 of SEQ ID NO: 1.

In another embodiment, a pharmaceutical composition comprises two anti-TNF monomer-specific antibodies or ligands. In one embodiment, the composition comprises an antibody or ligand that specifically binds the A2 epitope PSDKPVAH, amino acids 8-15 of SEQ ID NO: 1 or PSDKVPAHV, amino acids 8-16 of SEQ ID NO: 1 and an antibody or ligand that specifically binds the F epitope having the sequence EPIYLGGVF.

In yet a further embodiment, a pharmaceutical composition containing a bispecific antibody that specifically binds with the A2 epitope and the F epitope is also useful in interfering with soluble TNF trimer formation. Other forms of multi-ligand constructs known to the art may also take advantage of binding to A2 and/or F epitopes to provide trimer disruption. Alternatively, the anti-TNF monomer-specific compositions of this invention may be used in conjunction with, or sequentially with, other therapies or pharmaceutical regimens which are used conventionally to treat the various diseases mediated by sTNF.

These pharmaceutical compositions described herein also contain one or more pharmaceutically acceptable carriers or diluents. As defined herein, the pharmaceutically acceptable carrier suitable for use in an immunogenic proteinaceous composition of the invention are well known to those of skill in the art. Such carriers include, without limitation, water, saline, buffered saline, phosphate buffer, alcoholic/aqueous solutions, emulsions or suspensions. Other conventionally employed diluents, adjuvants and excipients, may be added in accordance with conventional techniques. Such carriers can include ethanol, polyols, and suitable mixtures thereof, vegetable oils, and injectable organic esters. Buffers and pH adjusting agents may also be employed. Buffers include, without limitation, salts prepared from an organic acid or base. Representative buffers include, without limitation, organic acid salts, such as salts of citric acid, e.g., citrates, ascorbic acid, gluconic acid, carbonic acid, tartaric acid, succinic acid, acetic acid, or phthalic acid, Tris, trimethanmine hydrochloride, or phosphate buffers. Parenteral carriers can include sodium chloride solution, Ringer's dextrose, dextrose and sodium chloride, lactated Ringer's or fixed oils. Intravenous carriers can include fluid and nutrient replenishers, electrolyte replenishers, such as those based on Ringer's dextrose and the like. Preservatives and other additives such as, for example, antimicrobials, antioxidants, chelating agents, inert gases and the like may also be provided in the pharmaceutical carriers. The present invention is not limited by the selection of the carrier. The preparation of these pharmaceutically acceptable compositions, from the above-described components, having appropriate pH isotonicity, stability and other conventional characteristics is within the skill of the art. See, e.g., texts such as Remington: The Science and Practice of Pharmacy, 22nd ed, Lippincott Williams & Wilkins, publ., 2012; and The Handbook of Pharmaceutical Excipients, 7th edit., eds. R. C. Rowe et al, Pharmaceutical Press, 2012.

III. Methods of Use

A. Treatment of Certain Inflammatory Conditions

A method for treating a mammalian, preferably human, subject having a disease mediated by soluble human TNF (sTNF) involves reducing the amount, concentration or bioactivity of sTNF in the blood of a subject having the disease without affecting the amount, concentration or bioactivity of tmTNF. This reduction occurs by disrupting, preventing or reducing the in vivo assembly or reassembly of dissociated monomers of TNF into bioactive trimeric human sTNF. Thus, in one embodiment, this method comprises administering to a subject in need thereof an isolated or synthetic anti-TNF monomer-specific antibody or ligand that specifically binds to an epitope of a dissociated monomer of TNF. The selected antibodies or ligands do not bind intact bioactive sTNF trimer. The selected antibody or ligand does not bind transmembrane TNF (tmTNF) and does not affect the structure or bioactivity of tmTNF.

In one embodiment, the method is useful for the treatment of rheumatoid arthritis. In another embodiment, the method is useful for the treatment of ankylosing spondylitis. In another embodiment, the method is useful for the treatment of juvenile rheumatoid arthritis. In still another embodiment, the method is useful for the treatment of psoriatic arthritis. In still another embodiment, the method is useful for the treatment of psoriasis. In another embodiment, the method is useful for the treatment of a pathogenic effect of bioactive, trimeric sTNF produced during inflammation or during the course of an inflammatory disorder. Still additional embodiments of the methods of the invention involve treatment of other diseases in which sTNF and/or inflammation at low or chronic levels plays a role. In one embodiment, such a disease is HIV-1. In another embodiment, the methods are useful for treating type 2 diabetes. In still other embodiment, the therapeutic selective anti-TNF monomer-specific antibodies or ligands are useful in methods for treating inflammation in the pathology of obesity. In another embodiment, the method is useful for the treatment of metabolic syndrome. In another embodiment, the method is useful for the treatment of atherosclerosis and associated cardiovascular disease. In another embodiment, the method is useful for the treatment of inflammation involved in the pathology of Alzheimer's disease. In another embodiment, the method is useful for the treatment of inflammation involved in the pathology of neurodegenerative diseases. Still other inflammatory diseases[40] may be treated with the compositions and methods described herein. Such treatment is not burdened by the immune suppression and morbidity and mortality associated with non-selective agents.

Therefore, in one embodiment the antibody/ligand useful in the method binds the A2 epitope sequence PSDKPVAH or PSDKPVAHV. In another embodiment of the method, the antibody/ligand useful in the method binds the F epitope EPIYLGGVF. The binding of the antibody/ligand to these selected epitopes disrupts or prevents assembly of the monomer into bioactive trimeric human sTNF. In still further embodiments of this method, the subject is administered two of these selective anti-TNF monomer-specific antibodies/ligands. In still other embodiments, the pharmaceutical compositions may include the bispecific antibodies discussed above.

Another aspect of this method involves maintaining a reduced amount or concentration of bioactive trimeric sTNF in the subject's bloodstream over time. Such maintenance can involve repeated administration of one of more of the above-noted selective anti-TNF monomer-specific antibodies, ligands, monoclonal antibodies, bispecific antibodies or pharmaceutical compositions containing same. By use of these methods, the subject's susceptibility to infection by an intracellular pathogen, e.g., tuberculosis, bacterial sepsis, invasive fungal infection, or histoplasmosis, or to a malignancy, e.g., lymphoma or hepatosplenic T-cell lymphoma, is not increased by treatment.

According to these therapeutic methods, the selective anti-TNF monomer-specific antibody or ligand is present in a pharmaceutical composition in a pharmaceutically acceptable carrier or diluent. Any of the pharmaceutical compositions described above, e.g., containing one or two of the antibodies/ligands, and possibly antibodies directed to non-sTNF immunogens, can be employed.

In each of the above-described methods, these compositions of the present invention are administered by an appropriate route, e.g., by the subcutaneous, mucosal, intravenous, intraperitoneal, intramuscular, nasal, or inhalation routes. The presently preferred route of administration is subcutaneous, intravenous or intramuscular.

The amount of the selective anti-TNF monomer-specific antibody, ligand, monoclonal or bispecific antibodies, or constructs described above, with or without other antibodies or ligands to other immunogens, present in each dose, is selected with regard to consideration of the patient's age, weight, sex, general physical condition and the specific disease being treated. The amount of antibody required to produce an exogenous effect in the patient without significant adverse side effects varies depending upon the pharmaceutical composition employed. In patients with a disease medicated by sTNF, generally, each dose will comprise between about 5 to 400 mg/mL injection of the selective anti-TNF monomer-specific antibody in a sterile solution. Another dosage is about 200 mg/mL of the antibody. Still another dosage is about 100 mg/mL of the antibody. Still another embodiment is a dosage of about 50 mg/mL of the antibody. A further embodiment is a dosage of about 10 mg/mL of the antibody. When used together, dosages of each anti-TNF monomer-specific antibody to a different one of the two monomer-specific TNF epitopes may be the same. In another embodiment, due to the synergy between the two combined selected anti-TNF monomer-specific antibodies, a combination dosage is lower than additive single dosages of each antibody alone. For example, the dosage of a bi-specific antibody directed to A2 and F may be less than the dosage of an antibody to one of these epitopes alone. Additional combination with antibodies directed to other than sTNF epitopes may alter the dosage of the anti-TNF monomer-specific antibodies.

In one embodiment, the administration of the selective anti-TNF monomer-specific antibody/ligand is repeated periodically during the course of the disease. In various embodiments in which two of the selective anti-TNF monomer-specific antibodies are administered in the course of treatment, each antibody/ligand in a pharmaceutically acceptable carrier is administered, either separately, in combination, or sequentially in any order.

The frequency of administration may range from weekly to monthly or bimonthly, and less frequently, and may depend upon the half-life of the antibody and the course of the particular disease. In one embodiment, the dosage is administered once a week. In another embodiment, the dosage is administered once every two weeks. In another embodiment the dosage is administered once a month. In another embodiment, the frequency of dosage administration is once every two or three months. Other dosage ranges may also be contemplated by one of skill in the art, particularly where administration of the antibody composition is in conjunction or sequential with other treatments for the disease.

B. Treatment of HIV-1 Infection

In still another aspect, a method for treating a subject to reduce or prevent re-infection or rebound infection with latent HIV-1 in a subject treated with anti-retroviral drugs is provided. According to this method, a subject receiving ART is administered the isolated or synthetic selective anti-TNF monomer-specific antibody or ligand, monoclonal antibody or bispecific antibody to epitopes A2 or F, or pharmaceutical composition containing same. In one embodiment, an anti-TNF monomer-specific antibody that binds A2 or F epitope is administered to a subject receiving anti-retroviral therapy. In another embodiment, an anti-TNF monomer-specific antibody or ligand or composition that binds A2 or F epitope is administered to a subject starting immediately after ART is discontinued. In still another embodiment, the anti-TNF monomer-specific antibodies/ligands/compositions are administered chronically to a subject both before ART treatment is discontinued and chronically after ART treatment is discontinued. The purpose of this method of treatment is to prevent re-infection or rebound infection of the subject with a different latent strain or variant of HIV after ART has successfully controlled the initial HIV infection.

In still other embodiments, the selective anti-TNF monomer-specific antibodies/ligands may be used in concert with other anti-HIV compositions (see e.g., U.S. Pat. No. 7,943,140).

According to any of the above methods, the selective anti-TNF monomer-specific antibody/ligands are administered in a pharmaceutically acceptable carrier, either separately, in combination, or sequentially in any order. The compositions, dosages, routes of administration and frequency of administration are anticipated to be as described. However, one of skill in the art, given the teachings of this application may employ other suitable dosages and routes of administration. Particularly for HIV, the administration of the selective anti-TNF monomer-specific antibody/ligand/ compositions is expected to be repeated periodically for an indefinite period.

C. Treatment of Diabetes

In still another aspect, sTNF elevations are also implicated in type II diabetes. Yet a further embodiment of this invention involves a method for treating diabetes which may also be practiced utilizing the selective anti-TNF monomer-specific antibodies and pharmaceutical compositions described herein. In one embodiment, this method for treating a human subject with type II diabetes comprises administering periodically to a subject in need thereof an isolated or synthetic selective anti-TNF monomer-specific antibody or ligand, or pharmaceutical composition. The antibody, ligand or pharmaceutical composition may be any of those described specifically above. In one embodiment, the subject is concurrently treated with other diabetes medication. In still another embodiment, the administration of the selective anti-TNF monomer-specific antibody/ligand or composition is repeated periodically after the subject ceases treatment with other diabetes medications, such as insulin or oral drugs such as metformin.

IV. Examples

The following examples illustrate certain embodiments of the above-discussed compositions and methods. These examples do not limit the disclosure of the claims and specification.

Example 1

TNF Epitope Mapping

The 157 amino acid TNF monomers SEQ ID NO: 1 have an elongated, anti-parallel β pleated sheet structure. When three monomers are associated in a non-covalent trimer, bioactive sTNF is formed. Five stretches of amino acid sequences form the interface β sheet contact surfaces:

| | | |
|---|---|---|
| A | KPVAHVVA, | aa11-18 of SEQ ID NO: 1; |
| A' | ALLAN, | aa35-39 of SEQ ID NO: 1; |
| C | GLYLIYSQVLFKGQ, | aa54-67 of SEQ ID NO: 1; |
| F | WYEPIYLGGVFQL, | aa114-126 of SEQ ID NO: 1; and |
| H | QVYFGIIAL, | aa149-157 of SEQ ID NO: 1, | where A, A', C, F and H refer to a β sheet naming convention[11].

To attain trimer disruption immunologically, the inventor theorized that antibody binding to epitope sequences that are wholly or partially within the contact area between adjacent monomers (the so-called internal or interface regions) would not bind to intact trimers of sTNF or tmTNF but would only bind to free monomers of TNF. In binding only to the free monomers, these antibodies would disrupt or prevent the ability of the monomers to re-associate and form active trimers.

Therefore, the inventor explored all five regions for potential B cell epitopes and detected and mapped antibodies to two epitopes partially (the A interface β sheet contact surface) and one epitope fully (the F interface β sheet contact surface) within an interface region. Rats or mice were immunized with synthetic peptides derived from the linear sequence from the five known interface regions of TNF identified above[5]. These synthetic peptides sequences were conjugated with KLH, and adjuvants such as Freunds Complete or Incomplete Adjuvant were used. Alternatively the synthetic peptide sequences are incorporated in self adjuvanting constructs, such as those described for HIV Tat constructs.[33] Polyclonal antibodies isolated from rats immunized with each of the synthetic peptide sequences were evaluated on rTNF and also on the synthetic TNF peptides using conventional ELISAs. See, e.g., the protocols described for anti-human TNF/TNFSF1A antibody by R&D Systems, catalog number MAB610, clones 28401, pages 1 and 2 (Jun. 17, 2005).

Binding to truncated sequences from larger peptide immunogens was used to delineate epitope margins. When antibodies were detected to a region of TNF, truncated peptide sequences were used to determine the margins of the epitopes defined above. An antibody that bound exclusively to one of each the specific epitope sequences was referred to as a selective anti-TNF monomer-specific antibody of this invention. See, e.g., FIG. 1.

Table 1 sets out the interface regions, immunogens tested and epitopes detected from the epitope searches:

TABLE 1

| Interface Region | Immunogens of SEQ ID NO: 1 Tested | Epitopes Detected* | Titers |
|---|---|---|---|
| A | aa1-15 and aa1-24 | aa4-12: SSRTPSDKP (epitope A1)<br>aa8-15: PSDKPVAH (epitope A2) | 400,000 to 1 million |
| A' | aa35-39 | No significant antibody response | — |
| C | aa52-67 | No significant antibody response | — |
| F | aa112-128 | aa116-124: EPIYLGGVF (epitope F) | 50,000 to 100,000 |
| H | aa145-157 | No significant antibody response | — |

Bold amino acids within interface sequences

FIGS. 2A, 2B and 2C illustrate the margin identification of the epitopes.

All three epitope sequences are outside of the known regions of the receptor binding sites of TNF[12,13,15]. The two overlapping B cell epitopes detected in synthetic peptide sequences overlapping interface contact region A are:

PSDKPVAH, amino acids 8-15 of SEQ ID NO: 1 and PSDKPVAHV, amino acids 8-16 of SEQ ID NO: 1; and SSRTPSDKP, amino acids 4-12 of SEQ ID NO: 1.

Thus, the sTNF aa1-23 sequence of SEQ ID NO: 1 contains only two B cell epitopes, each epitope containing interface amino acid(s) essential for antibody binding, but only epitope A2 contains amino acids necessary for trimer formation and biological function.

The entire sequence of the third epitope EPIYLGGVF (F sheet), amino acids 116-124 of SEQ ID NO: 1 was within interface contact region F. Two of the epitope amino acids, $Tyr_{119}$ and $Gly_{122}$, are critical for trimer formation and biological activity[13,24].

In the three epitopes shown above, the bolded amino acids are within the internal interface regions. The italicized amino acids are those at which point mutations induce failure to form trimers and loss of biological activity.

Antibodies to each of three monomer-specific epitopes A1: SSRTPSDKP, A2: PSDKPVAH/PSDKVPAHV and F: EPIYLGGVF bind to synthetic rTNF (which comprises trimer, dimer and monomer forms) in the conventional ELISA assay. Antibodies to A1 SSRTPSDKP (both polyclonal antibodies and monoclonal antibodies) bound only two interface amino acids ($Lys_{11}$ and $Pro_{12}$), essential for antibody binding to the epitope. Neither of these amino acids have been shown to be critical for trimer formation and bioactivity of sTNF. Antibodies to A2 PSDKPVAH or PSDKPVAHV (both polyclonal antibodies and monoclonal antibodies) also masked $His_{15}$ that is critical to trimer formation and bioactivity of sTNF molecules[13,23].

Only one other monomer specific antibody was detected, within the F monomer interface region. The F epitope spanned TNF amino acids 116-124 and induced polyclonal antibodies that were monomer-specific. These antibodies masked $Tyr_{119}$ and $Gly_{122}$, both critical to trimer formation and bioactivity of sTNF molecules.

Example 2

Selective Binding Activity

Natural or synthetic sTNF consists of a mixture of inactive TNF monomers, inactive TNF dimers and bioactive TNF trimers. Each antibody used in the assays and commercially available anti-TNF antibodies (e.g., REMICADE) or commercially available TNF receptor chimera (e.g., ENBREL) binds to synthetic TNF coated on a plate, as in the conventional ELISAs performed in Example 1. However, detection of specific binding of an antibody/ligand to the monomeric, dimeric or trimeric form of sTNF requires appropriate selective assays. To demonstrate the selective binding activity of antibodies or ligands that bind only the three epitopes on a monomer as identified in Example 1, the following assays are performed:

A. Sandwich Assay

In one embodiment, a sandwich assay employs a biotinylated anti-TNF antibody which binds the sTNF in a sample, followed by detection with the same antibody, non-biotinylated, coated on a plate[25]. The unlabeled antibody is plated (e.g., one of the inventor's epitope-binding antibodies or a commercial antibody, e.g., REMICADE antibody). A sample containing synthetic sTNF mixed with the same anti-TNF antibody, which has been biotinylated, is prepared and then introduced to the plate. The plate is then washed and any bound sTNF sandwiched between the unlabeled bound antibody and the labeled detector antibody is measured using a suitable detector system, e.g., streptavidin/horseradish peroxidase, to generate a detectable signal.

If the antibody used as the capture/detector antibody is an antibody that binds sTNF trimeric form, a sandwich effect will be detected. Only sTNF trimers with the ability to simultaneously bind both the plate-bound antibody and the biotinylated antibody will demonstrate binding in this assay. This is because in the mixture not all binding sites on the trimers will be bound, thereby leaving extra binding sites to be captured on the plate. For example, the commercial REMICADE antibody demonstrates trimer binding in this assay.

In contrast, the inventor's antibodies that specifically bind a single epitope on a sTNF monomer do not demonstrate binding in this assay. Once each monomer is bound by the labeled antibody in the mixture, that epitope is no longer available for binding to the same unlabeled antibody on the plate when the mixture is added to the plate. A sandwich cannot form.

This assay can therefore be used to distinguish between the anti-TNF monomer-specific antibodies/ligands that bind to A2 or F selectively and that bind only sTNF monomers and those non-selective commercial and known anti-TNF antibodies that bind trimers, both tm-TNF and trimeric sTNF.

When employed in these assays, the inventor determined that antibodies (both polyclonal or monoclonal) to epitopes A1, A2 or F all were able to bind only sTNF monomers. Results from performance of this assay are shown in FIGS. 3A and 3B.

B. Functional Assay

A functional assay is one that demonstrates the effects of the antibodies on TNF binding cells, such as actinomycin treated WEHI cells. See, e.g., the protocols for "Neutralization of Human TNF Bioactivity" described for anti-human TNF/TNFSF1A antibody by R&D Systems, catalog number MAB610, clones 28401, pages 1 and 2 (Jun. 17, 2005), incorporated by reference herein. For the generation of the data in FIGS. 4B and 5, in place of the cells L929, WEHI cells are used. This assay showed inhibition of TNF activity by the selected tested antibodies. In this assay the antibodies that bind one of the three epitopes on the monomers as described herein are evaluated to determine if they have the ability to disrupt the formation of bioactive trimers of sTNF and thus inhibit sTNF activity in a dose response curve. Performance of this functional assay and its results are demonstrated in FIGS. 4B and 5.

C. Results

In the sandwich assay described above, the selective antibodies that bound one of the three epitopes on the sTNF monomer: A1: SSRTPSDKP, A2: PSDKPVAH or PSDKPVAHV and F: EPIYLGGVF, bound only the monomeric form of sTNF. As described above, the biotinylated selective anti-TNF antibodies that bind one of the epitopes A1, A2 or F would not sandwich with sTNF to cause binding by the same selective non-biotinylated anti-TNF monomer-specific antibody coated plate. See, e.g., FIGS. 3A and 3B. In contrast to the results for the anti-A2 and anti-F antibodies/ligands, the commercial anti-TNF REMICADE antibody demonstrated binding in the sandwich assay (see e.g., FIG. 3), showing binding to trimeric TNF. Additionally all polyclonal antibodies to TNF peptides encroaching an interface region were negative in the sandwich assay, showing lack of binding to trimers, demonstrating that binding was restricted to monomers.

However, only two of the antibodies that exhibited selective binding to one of the three epitopes, A1: SSRTPSDKP, A2: PSDKPVAH and F: EPIYLGGVF, produced dose-responsive inhibition of TNF, suppression of TNF inhibition of cell replication in actinomycin treated WEHI cells in the functional assay. See, e.g., FIGS. 4A, 4B and 5. Antibodies to A2 and F were capable of disrupting trimer formation and were associated with inhibition of sTNF binding to TNF receptors and inhibition of cytotoxicity of sTNF on actinomycin treated WEHI cells. These assay findings provided evidence that the monomer specific antibodies to epitopes A2 and F disrupt trimer assembly by blocking specific amino acid side chains essential for inter-monomer binding.

Surprisingly, antibodies to the A1 epitope, while monomer specific, were inactive in blocking TNF function.

Throughout this specification, the words "comprise", "comprises", and "comprising" are to be interpreted inclusively rather than exclusively. The words "consist", "consisting", and its variants, are to be interpreted exclusively, rather than inclusively. It should be understood that while various embodiments in the specification are presented using "comprising" language, under various circumstances, a related embodiment is also be described using "consisting of" or "consisting essentially of" language. It is to be noted that the term "a" or "an", refers to one or more, for example, "an antibody" is understood to represent one or more antibodies. As such, the terms "a" (or "an"), "one or more," and "at least one" is used interchangeably herein.

Unless defined otherwise in this specification, technical and scientific terms used herein have the same meaning as commonly understood by one of ordinary skill in the art to which this invention belongs and by reference to published texts, which provide one skilled in the art with a general guide to many of the terms used in the present application. All documents listed or referred to herein, including U.S. provisional applications Nos. 61/768,044 and 61/756,571, as well as the attached or electronic Sequence Listing, are incorporated herein by reference.

Given the teachings provided in this specification, one of skill in the art can generate antibodies and other antibody fragments, including high affinity polyclonal antibodies, affinity purified and humanized antibodies, monoclonal antibodies and bispecific antibodies that bind specifically to one or more of the epitopes A2 or F by conventional methodologies. Such antibodies and ligands are readily obtained and useful in the methods disclosed herein. Without further description, it is believed that one of ordinary skill in the art can, using the preceding description and the following illustrative examples, make and utilize the compositions of the present invention and practice the claimed methods. While the invention has been described and illustrated herein by references to various specific materials, procedures and examples, it is understood that the invention is not restricted to the particular combinations of material and procedures selected for that purpose. Numerous modifications and variations of the embodiments illustrated above are included in this specification and are expected to be obvious to one of skill in the art. Such modifications and alterations to the compositions and processes described herein are believed to be encompassed in the scope of the claims appended hereto.

REFERENCES

1. Taylor, P. C. & Feldmann, M. Anti-TNF biologic agents: still the therapy of choice for rheumatoid arthritis. Nature reviews. Rheumatology 5, 578-582 (2009).
2. Feldmann, M. & Maini, R. N. Anti-TNF therapy, from rationale to standard of care: what lessons has it taught us? J Immunol 185, 791-794 (2010).
3. Wallis, R. S., et al., Granulomatous infectious diseases associated with tumor necrosis factor antagonists. Clinical infectious diseases: an official publication of the Infectious Diseases Society of America 38, 1261-1265 (2004).
4. Bongartz, T., et al. Anti-TNF antibody therapy in rheumatoid arthritis and the risk of serious infections and malignancies: systematic review and meta-analysis of rare harmful effects in randomized controlled trials. JAMA: the journal of the American Medical Association 295, 2275-2285 (2006).
5. Scallon, B. J., et al., Chimeric anti-TNF-alpha monoclonal antibody cA2 binds recombinant transmembrane TNF-alpha and activates immune effector functions. Cytokine 7, 251-259 (1995).
6. Mitoma, H., et al. Infliximab induces potent anti-inflammatory responses by outside-to-inside signals through transmembrane TNF-alpha. Gastroenterology 128, 376-392 (2005).
7. Olleros, M. L., et al. Transmembrane TNF induces an efficient cell-mediated immunity and resistance to Mycobacterium bovis bacillus Calmette-Guerin infection in the absence of secreted TNF and lymphotoxin-alpha. J Immunol 168, 3394-3401 (2002).
8. Li, Q., et al. Mechanism of action differences in the antitumor effects of transmembrane and secretory tumor necrosis factor-alpha in vitro and in vivo. Cancer immunology, immunotherapy: CII 55, 1470-1479 (2006).
9. Alexopoulou, L., et al. Transmembrane TNF protects mutant mice against intracellular bacterial infections, chronic inflammation and autoimmunity. European journal of immunology 36, 2768-2780 (2006).
10. Smith, R. A. & Baglioni, C. The active form of tumor necrosis factor is a trimer. The Journal of biological chemistry 262, 6951-6954 (1987).
11. Eck, M. J. & Sprang, S. R. The structure of tumor necrosis factor-alpha at 2.6 A resolution. Implications for receptor binding. The Journal of biological chemistry 264, 17595-17605 (1989).
12. Van Ostade, X., et al., Localization of the active site of human tumour necrosis factor (hTNF) by mutational analysis. The EMBO journal 10, 827-836 (1991).
13. Zhang, X. M., et al., Site-directed mutational analysis of human tumor necrosis factor-alpha receptor binding site and structure-functional relationship. The Journal of Biological Chemistry 267, 24069-24075 (1992).
14. Yang, Z., et al., Crystal structure of TNFalpha complexed with a poxvirus MHC-related TNF binding protein. Nature Structural & Molecular Biology 16, 1189-1191 (2009).
15. Mukai, Y., et al. Solution of the structure of the TNF-TNFR2 complex. Science Signaling 3, ra83 (2010).
16. Tang, P., et al., Human pro-tumor necrosis factor is a homotrimer. Biochemistry 35, 8216-8225 (1996).
17. Utsumi, T., et al. Transmembrane TNF (pro-TNF) is palmitoylated. FEBS letters 500, 1-6 (2001).
18. Corti, A., et al. Oligomeric tumour necrosis factor alpha slowly converts into inactive forms at bioactive levels. The Biochemical Journal 284 (Pt 3), 905-910 (1992).
19. Steed, P. M., et al. Inactivation of TNF signaling by rationally designed dominant-negative TNF variants. Science 301, 1895-1898 (2003).
20. Zalevsky, J., et al. Dominant-negative inhibitors of soluble TNF attenuate experimental arthritis without suppressing innate immunity to infection. J Immunol 179, 1872-1883 (2007).
21. He, M. M., et al. Small-molecule inhibition of TNF-alpha. Science 310, 1022-1025 (2005).
22. Wells, J. A. & McClendon, C. L. Reaching for high-hanging fruit in drug discovery at protein-protein interfaces. Nature 450, 1001-1009 (2007).
23. Yamamoto, R., et al., Histidine-15: an important role in the cytotoxic activity of human tumor necrosis factor. Protein engineering 2, 553-558 (1989).
24. Douni, E., et al. A RANKL G278R mutation causing osteopetrosis identifies a functional amino acid essential for trimer assembly in RANKL and TNF. Human Molecular Genetics 21, 784-798 (2012).
25. Nagahira, K., et al. Epitope mapping of monoclonal antibodies to tumor necrosis factor-alpha by synthetic peptide approach. Immunology Letters 46, 135-141 (1995).

26. Socher, S. H., et al. Antibodies against amino acids 1-15 of tumor necrosis factor block its binding to cell-surface receptor. Proceedings of the National Academy of Sciences of the United States of America 84, 8829-8833 (1987).
27. Chackerian, B., et al., Conjugation of a self-antigen to papillomavirus-like particles allows for efficient induction of protective autoantibodies. The Journal of Clinical Investigation 108, 415-423 (2001).
28. Spohn, G., et al. A virus-like particle-based vaccine selectively targeting soluble TNF-alpha protects from arthritis without inducing reactivation of latent tuberculosis. J Immunol 178, 7450-7457 (2007).
30. Fee, C. J., Protein conjugates purification and characterization, PEGylated Protein Drugs: Basic Science and Clinical Applications, Veronese, F. M., Ed. Birkhauser Publishing: Basel, 113-125 (2009).
31. Fee, C. J.; and Damodaran, V. B., Production of PEGylated Proteins, in Biopharmaceutical Production Technology, G. Subramanian, Ed. Wiley-VCH Verlag GmbH & Co. KGaA, Weinheim, Germany (2012).
32. Harlow, E. and Lane, D. (1988). Antibodies: A Laboratory Manual. Cold Spring Harbor, N.Y.: Cold Spring Harbor Laboratory.
33. Goldstein, G. and Chicca, JJ, A universal anti-HIV-1 Tat epitope vaccine that is fully synthetic and self-adjuvanting vaccine, Vaccine, 28:1008-1014 (December 2009).
34. Stacy, A R et al, Induction of a Striking Systemic Cytokine Cascade prior to Peak Viremia in Acute Human Immunodeficiency Virus Type 1 Infection, in Contrast to More Modest and Delayed Responses in Acute Hepatitis B and C Virus Infections, J. Virol., 83(8):3719-3733 (April 2009)
35. U.S. Pat. No. 7,227,003
36. U.S. Pat. No. 7,223,394
37. U.S. Pat. No. 7,070,775
38. U.S. Pat. No. 5,919,452
39. U.S. Pat. No. 5,698,419
40. Tabas, I. and Glass, CK, Anti-inflammatory Therapy in Chronic Disease: Challenges and Opportunities, Science, vol. 339:166 (January 2013)
41. Hornig N, Farber-Schwarz A., "Production of bispecific antibodies: diabodies and tandem scFv.", 2012, Methods Mol Biol., 907:713-27
42. Speiss, C. et al," Bispecific antibodies with natural architecture produced by co-culture of bacteria expressing two distinct half-antibodies, Jul. 7, 2013, Nature Biotechnology, 31:753-758
43. Jonathan S Martin and Zhenping Zhu, "Recombinant approaches to IgG-like bispecific antibodies", 2005 Acta Pharmacologica Sinica, 26: 649-658

What is claimed is:

1. A monoclonal antibody or a fragment of the antibody that specifically binds to an epitope on a dissociated monomer of human TNF, the epitope having the amino acid sequence EPIYLGGVF, amino acids 116 to 124 of SEQ ID NO: 1, said specific binding disrupting assembly of the monomer into bioactive trimeric human soluble TNF, without binding to intact bioactive trimeric human soluble TNF or trimeric transmembrane TNF.

2. The antibody or fragment according to claim 1, which is a single chain of an antibody, a recombinant antibody, a chimeric antibody, a humanized antibody, a human antibody, or a bi-specific antibody.

3. The antibody or fragment according to claim 2, wherein said antibody fragment is an sc-Fv construct, a Fab construct, a Fab$_2$ construct, or a construct containing a light chain or heavy chain variable or complementarity determining region (CDR) sequence.

4. A pharmaceutical composition consisting essentially of a monoclonal antibody or antigen-binding fragment thereof that specifically binds to an epitope on a dissociated monomer of human TNF, the epitope having the amino acid sequence EPIYLGGVF, amino acids 116 to 124, said specific binding disrupting assembly of the monomer into bioactive trimeric human soluble TNF, without binding to intact bioactive trimeric human soluble TNF or trimeric transmembrane TNF, and a pharmaceutically acceptable carrier or diluent.

5. The pharmaceutical composition according to claim 4, wherein the antibody or fragment is a single chain antibody, a recombinant antibody, a chimeric antibody, a humanized antibody, a human antibody, or a bi-specific antibody.

6. The pharmaceutical composition according to claim 4, wherein the antibody or fragment is an sc-Fv construct, a Fab construct, a Fab$_2$ construct, or a construct containing a light chain or heavy chain variable or complementarity determining region (CDR) sequene.

7. A method for treating a subject having Alzheimer's disease comprising administering to the subject in need thereof the monoclonal antibody or fragment of claim 1 effective to reduce the amount or concentration of bioactive trimeric sTNF in the blood without affecting the amount, concentration or bioactivity of tmTNF and to disrupt or reduce the in vivo assembly or reassembly of dissociated monomers of sTNF into bioactive trimeric human sTNF.

8. A method for treating a subject having a disease mediated by human TNF comprising administering to a subject in need thereof a monoclonal antibody or fragment thereof that specifically binds to an epitope on a dissociated monomer of human TNF, the epitope having the amino acid sequence EPIYLGGVF, amino acids 116 to 124 of SEQ ID NO: 1, said specific binding disrupting assembly of the monomer into bioactive trimeric human soluble TNF, without binding to intact bioactive trimeric human soluble TNF or trimeric transmembrane TNF, wherein said disease is rheumatoid arthritis, ankylosing spondylitis, juvenile rheumatoid arthritis, psoriatic arthritis, psoriasis, obesity, metabolic syndrome, atherosclerosis, cardiovascular disease, Alzheimer's disease or type II diabetes.

* * * * *